US007277167B2

(12) United States Patent
Schembri et al.

(10) Patent No.: US 7,277,167 B2
(45) Date of Patent: Oct. 2, 2007

(54) MODULAR CUVETTES AND METHODS FOR USE THEREOF

(75) Inventors: Carol T. Schembri, San Mateo, CA (US); Zhenghua Ji, Wilmington, DE (US); Hongfeng Yin, Cupertino, CA (US); William H. McAllister, Saratoga, CA (US)

(73) Assignee: AGilent Technologies, Inc., Santa Clara, CA (US)

( * ) Notice: Subject to any disclaimer, the term of this patent is extended or adjusted under 35 U.S.C. 154(b) by 56 days.

(21) Appl. No.: 11/225,743

(22) Filed: Sep. 13, 2005

(65) Prior Publication Data

US 2007/0201021 A1    Aug. 30, 2007

(51) Int. Cl.
*G01N 21/03* (2006.01)
(52) U.S. Cl. ...................................... 356/246
(58) Field of Classification Search ............... None
See application file for complete search history.

(56) References Cited

U.S. PATENT DOCUMENTS

| 3,720,354 | A | 3/1973 | Drummond et al. |
| 3,828,987 | A | 8/1974 | Drummond et al. |
| 4,643,580 | A | 2/1987 | Gross et al. |
| 4,681,443 | A | * 7/1987 | Bach et al. ................. 356/246 |
| 4,910,402 | A | 3/1990 | McMillan |
| 4,991,958 | A | 2/1991 | Garner |
| 5,416,879 | A | 5/1995 | Liu |
| 5,444,807 | A | 8/1995 | Liu |
| 5,460,782 | A | 10/1995 | Coleman et al. |
| 5,674,457 | A | 10/1997 | Williamsson et al. |
| 5,815,258 | A | 9/1998 | Nakanishi |
| 5,844,686 | A | 12/1998 | Treptow et al. |
| 6,104,485 | A | 8/2000 | Wang et al. |
| 6,214,626 | B1 | 4/2001 | Meller et al. |
| 6,396,584 | B1 | 5/2002 | Taguchi et al. |
| 6,541,266 | B2 | 4/2003 | Modzelewski et al. |
| 6,618,137 | B1 | * 9/2003 | Sawa et al. ................. 356/246 |
| 6,628,382 | B2 | 9/2003 | Robertson |
| 2002/0058342 | A1 | 5/2002 | Lilja et al. |
| 2002/0136667 | A1 | 9/2002 | Subramanian et al. |
| 2002/0140931 | A1 | 10/2002 | Robertson |
| 2002/0154299 | A1 | 10/2002 | Robertson |

FOREIGN PATENT DOCUMENTS

EP    0158948    4/1985

* cited by examiner

*Primary Examiner*—Tu T. Nguyen

(57) ABSTRACT

An apparatus for holding liquid samples.

29 Claims, 8 Drawing Sheets

SECTION A-A

MODULAR CUVETTES AND METHODS FOR USE THEREOF

BACKGROUND OF THE INVENTION

There are many use environments, the fields of medical research and pharmaceutical development being examples, where it is necessary to accurately acquire fluid samples with volumes that may be as small as a few nanoliters. In these same fields, it is also often desirable to measure optical characteristics of the acquired fluid samples. Such optical characteristics include, for example, the ability of a sample to absorb light.

For instance, UV-Visible Spectrophotometry may be used to characterize the chemical composition of a liquid sample (in solution or suspension phase) using the absorbed spectra of the sample. The light absorbance of a sample depends on the pathlength L of light passing through the sample, as well as on the concentration of light absorbers (e.g., biomolecules, cells, etc) in a sample solution and the wavelength ($\lambda$) of light being used to characterize the sample. The wavelengths of UV-Visible light span from 200 nm to 800 nm, while ultraviolet wavelengths range from 200 to 400 nm.

UV-Visible spectrophotometry provides a convenient analysis technique to determine the concentration, purity, and integrity of a biological sample without requiring additional sample preparation other than acquiring a sample. UV-Visible Spectrophotometry measurements depend on the light source (UV lamp), the sample and sampling technique. Most biological samples absorb electromagnetic radiation at wavelengths ranging from 200 nm to 800 nm, mostly 230, 260 and 280 nm. For a DNA or RNA sample in aqueous phase, one unit of absorbance 1 Å measured at a $\lambda 260$ nm and a pathlength of 10 mm is equal to 50/(40) ng/ml concentration.

Most biological samples are highly concentrated for downstream processing (such as microarray spotting or protein sample preparation for mass spectrometers). The absorbance of such samples can be above the saturation limit for typical spectrophotometers if the pathlength is about 10 mm. While the sample concentration range can be extended by diluting the sample, diluting a sample requires additional laboratory work and can result in errors. Other approaches are needed to extend the sample concentration range that can be evaluated by the instrument.

Sampling techniques used in conventional UV-Visible Spectrophotometers include utilizing a cuvette with an optical window and fixed optical pathlength that holds a sample in a semi-closed way, direct measurement of liquid sample in a sample container (e.g., a well) along with a real-time pathlength measurement, and using a cuvetteless sample held in semi-free space between optical fibers which define a light path from a light source to a detector.

The cuvette-based sampling technique is widely used in conventional UV-Visible spectrophotometers. Generally, a sample is pipetted into a cuvette that has either a 10 mm or 2 mm path length. This technique is very limited for most biological samples since cuvettes typically used generally require a minimum 10 ml sample, which is problematic for valuable biological samples which may be present in limiting quantities, such as samples of proteins or nucleic acids. A cuvette made of quartz or silica is expensive so it is typically reused after cleaning and drying. Further, adding 10 ml of sample with a pipette into a cuvette sometimes produces an air-bubble interface in the light path that can cause measurement error or void measurements. Additionally, a pathlength of 2 mm or 10 mm limits the sample concentration that may be measured to 1000 ng/ml for a DNA/RNA sample due to the limited dynamic range of absorbance of most spectrophotometers.

Direct UV-Visible spectrophotometry measurement of liquid samples also suffers from limitations, such as the need to determine pathlength and adjust sample concentration. Pathlength depends on the sample well dimensions and sample volume. The determination of pathlength requires use of instruments such as level detectors or position sensors. For a pathlength ranging from 2 mm to 10 mm or above, the workable range of sample concentration for a spectrophotometer measurement becomes limited. For an example, for a double stranded DNA sample, if the pathlength is 10 mm, one unit of absorbance is equal to 50 ng/ul concentration (OD), and the upper limit of detection is typically 250 ng/ul if the upper limit absorbance of the spectrophotometer is 5. In this case, sample dilution is required for a sample concentration greater than 250 ng/ul. Sample dilution for multiple well plate measurements can be a complex laboratory operation.

Cuvetteless sampling also suffers from drawbacks. For example, in cuvetteless sampling, typically a narrow beam of light is directed to a sample stage that consists of a 1-2 µl liquid droplet suspended between two multi-mode optical fibers, one source-side fiber which provides light from a light source to the droplet and a detection-side fiber that guides light from the droplet to appropriate detection optics. The close proximity between the source-side and detection-side fibers allows enough of the light cone emanating from the source-side fiber to be collected by the detection-side fiber after passing through a liquid sample.

Cuvetteless instruments typically require a clamping surface that can be wetted with sample to avoid an air-bubble interface. Carry-over contamination is not completely removed with a simple wiping-off of the clamping surface. Adding a small amount of sample (1 ml) to the center of the clamping surface is also a complicated lab technique.

In summary, existing sampling techniques used in the conventional UV-Visible Spectrophotometers generally require too much sample, provide insufficient confidence in the sample application technique, may result in carry-over contamination, and may require pathlength determination and/or dilution of sample, over a range of solution concentrations.

Additionally, the requirements of small sample collection, accurate path length determination, ease of handling and the ability to interface with other equipment pose conflicting demands on the design of any sample collection apparatus.

There is, therefore, a need for a sample collection apparatus that is capable of simultaneously meeting the conflicting demands.

BRIEF SUMMARY OF THE INVENTION

An embodiment of the apparatus for sample acquisition of this invention includes a first body having openings at opposite ends thereof, a second body having openings at opposite ends thereof, and a third body having openings at opposite ends thereof, each of the first body, second body, and third body having a respective passageway connecting the openings at opposite ends thereof, at least a portion of a surface of said second body being at least partially transparent to predetermined electromagnetic radiation and forming a measurement region with a predetermined optical pathlength, the first body being operatively connected to the second body and the second body being operatively connected to the third body to permit flow through the respective passageways thereof, and at least a portion of the third body being adapted to enable acquisition of a sample.

An embodiment of the method of this invention for providing an apparatus for holding a sample includes the steps of providing a first section of the apparatus, selecting a material, the material being at least partially transparent to predetermined electromagnetic radiation, providing a second section of the apparatus, at least a portion of the second section comprising the selected material, operatively connecting an end of the first section to an end of the second section in order to permit flow between the first section and the second section, providing a third section of the apparatus, adapting at least a portion of the third section to enable acquisition of a fluid sample from a sample supply, and operatively connecting another end of the second section to an end of the third section in order to permit flow between the second section and the third section.

BRIEF DESCRIPTION OF THE DRAWINGS

For a better understanding of the present invention, reference is made to the accompanying drawings and detailed description and its scope will be pointed out in the appended claims.

DETAILED DESCRIPTION OF THE INVENTION

Figure 1:
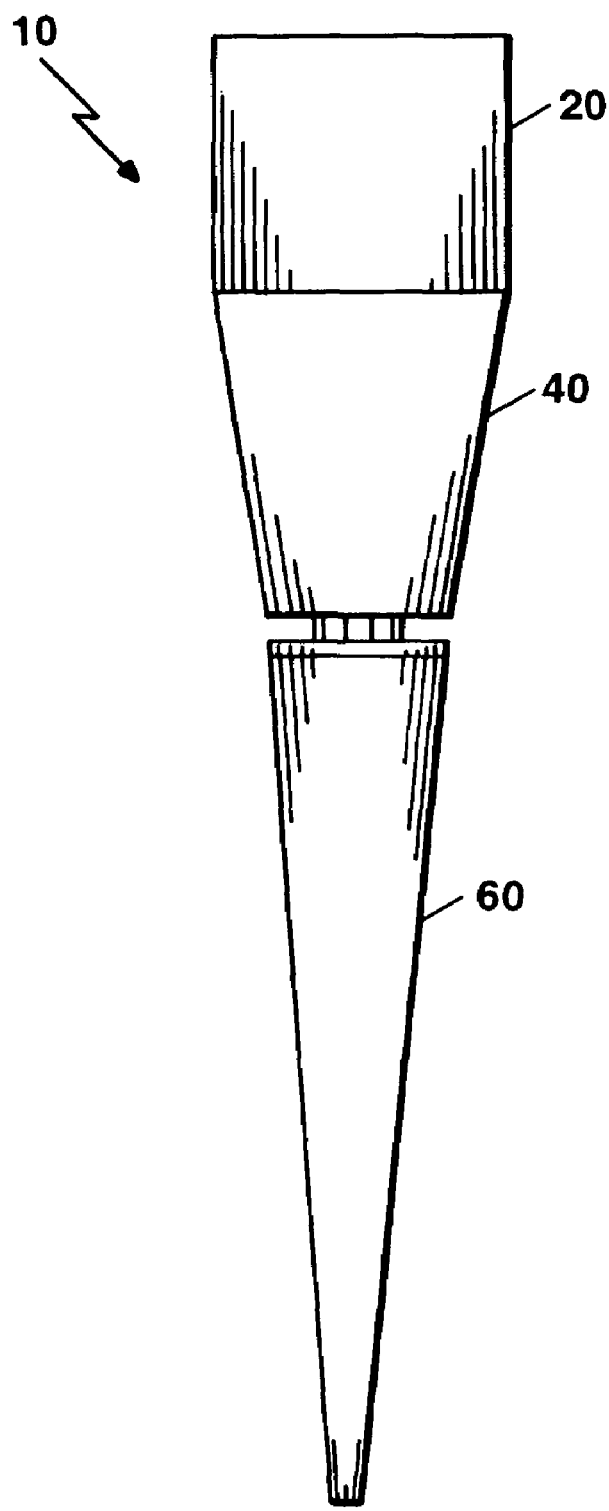
FIG. 1 is a schematic representation of an external view of an embodiment of the apparatus of this invention.

Before describing the present invention in detail, it is to be understood that this invention is not limited to specific apparatuses, method steps, or equipment, as such may vary. It is also to be understood that the terminology used herein is for the purpose of describing particular embodiments only, and is not intended to be limiting. Methods described herein may be carried out in any order of the recited steps that is logically possible. Furthermore, where a range of values is provided, it is understood that every intervening value, between the upper and lower limit of that range and any other stated or intervening value in that stated range is encompassed within the invention. Also, it is contemplated that any optional feature of the inventive embodiments and aspects described herein may be set forth and claimed independently, or in combination with any one or more of the features described herein, or may be specifically excluded.

Unless defined otherwise below, all technical and scientific terms used herein have the same meaning as commonly understood by one of ordinary skill in the art to which this invention belongs. Still, certain terms are defined herein for the sake of clarity.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed. All publications mentioned herein are incorporated herein by reference to disclose and describe the methods and/or materials in connection with which the publications are cited.

It must be noted that, as used in this specification and the appended claims, the singular forms "a", "an" and "the" include plural referents unless the context clearly dictates otherwise. Thus, for example, reference to "a biopolymer" includes more than one biopolymer, and the like.

It will also be appreciated that throughout the present application, that words such as "upper", "lower" are used in a relative sense only.

The term "assessing" and "evaluating" are used interchangeably to refer to any form of measurement, and includes determining if an element is present or not. The terms "determining," "measuring," and "assessing," and "assaying" are used interchangeably and include both quantitative and qualitative determinations. Assessing may be relative or absolute. "Assessing the presence of" includes determining the amount of something present, as well as determining whether it is present or absent.

The term "optical" as used herein refers to properties related to the entire spectrum of electromagnetic radiation.

The term "using" has its conventional meaning, and, as such, means employing, e.g. putting into service, a method or composition to attain an end.

An apparatus for holding small volume liquid samples with a predetermined pathlength is described hereinbelow.

Figure 2:
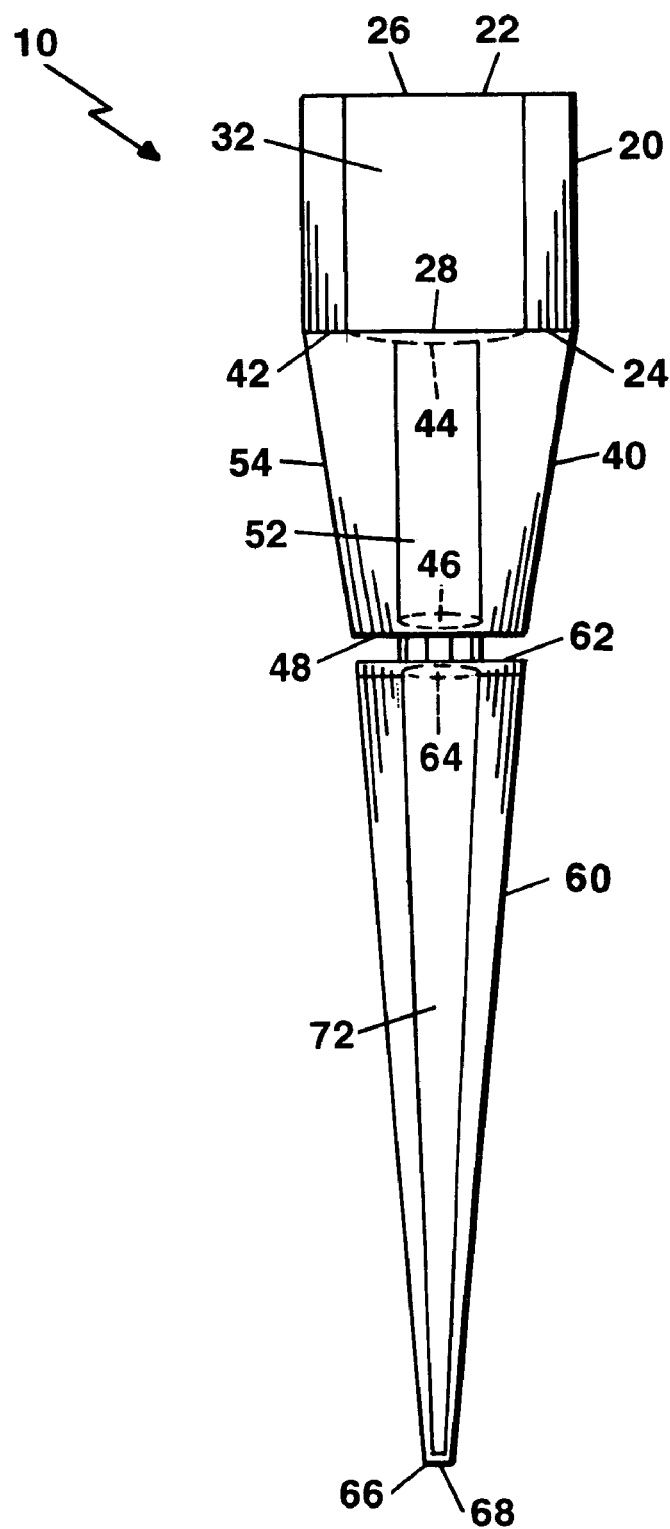
FIG. 2 is a schematic representation of an internal view of the embodiment shown in FIG. 1.

In one embodiment, shown in FIGS. 1 and 2, the apparatus 10 includes three bodies, a first body 20, a second body 40 and a third body 60. Each body 20, 40, 60 has openings at opposite ends. The first body 20 has a first opening 26 at the first end 22, a second opening 28 at a second end 24 and a passageway 32 connecting the first opening 26 to the second opening 28. The second body 40 has a first opening 44 at a first end 42, a second opening 46 at a second end 48 and a passageway 52 connecting the first opening 44 to the second opening 46. The third body has a first opening 64 at a first end 62, a second opening 68 and a second end 66, and a passageway 72 connecting the first opening 64 to the second opening 68. The first end 42 of the second body and the first opening 44 of the second body are capable of being operatively connected to the second end 24 of the first body and the second opening 28 of the first body. In one instance, the operative connection is capable of providing a substantially gastight connection between the first opening 44 of the second body and the second opening 28 of the first body. At least a portion of a surface 54 of the second body 40 is at least partially transparent to electromagnetic radiation in a given range of wavelengths. At least a portion of the passageway 52 of the second body forms a measurement region with a predetermined optical pathlength. The first end 62 of the third body and the first opening 64 of the third body are capable of being operatively connected to the second end 48 of the second body and the second opening 46 of the second body. In one instance, that operative connection is capable of providing a substantially gastight connection between the first opening 64 of the third body and the second opening 46 of the second body. At least a portion of the third body 60 is adapted to enable acquisition of a sample. The operative connections between the first body 20 and the second body 40 and between the second body 40 and the third body 60 permit flow through the respective passageways 32, 52, 72 thereof.

In one embodiment, the first end 22 of the first body 20 and the first opening 26 of the first body 20 are capable of operatively connecting to a device for aspirating fluid, e.g., such as a pipette (a "pipette" as used herein, unless otherwise specified, refers to that aspiration causing portion of a pipette e.g., such as a Pipetman®, a Gilson®, Rainin®, Eppendorf® or Finnipipette® pipette, and may also be referred to as "pipettor") or a rubber bulb, a fluid-delivery device, or to an interface to such a device (e.g., to a pipette tip). In operation, the device for aspirating fluid may be used for aspirating a liquid sample into one or a combination of the respective passageways 32, 52, or 72. In one instance, the material used in the first body 20 is a plastic which may be selected based on material and/or economic considerations.

In another embodiment, the first body 20 is constructed such that it allows a user to handle the apparatus manually.

In one instance, the third body 60 is constructed using injection-molded materials in order to provide a very narrow inlet which can be used to minimize sample volume. In another instance, the third body 60 is shaped such that it allows access to a sample container (for example, but not limited to, an Eppendorf® tube, a multi-well plate, etc.). In one aspect, an end of the third body for contacting a liquid sample is flat. In another aspect, the end is tapered or curved. In still another aspect, the end comprises a slit.

In one embodiment, the material used for the third body 60 is selected such that it has the appropriate hydrophobicity for the intended application. In one instance, a hydrophobic material would be appropriate to minimize the quantity of fluid remaining on the lower outside surface of the third body 60. By way of example, the body could be injection-molded, formed or machined from polypropylene, a polyolefin, fluoropolymer and the like. Alternatively, the parts could be coated with a hydrophobic coating. An exemplary embodiment of a hydrophobic coating material comprises a siloxane, for example. The coating may be polydimethylsiloxane silicon rubber, PTFE (e.g., Teflon®), a polyacrylate, and the like, but this invention is not limited to only these exemplary embodiments.

In another instance, which includes the application in which a protein-based sample is being evaluated, a hydrophilic material can be selected for the third body 60 in order to minimize protein binding. The material of appropriate hydrophobicity can comprise the entire third body 60 or a portion thereof.

In another embodiment, the passageway 72 of the third body 60 comprises a dimension sufficiently small to enable holding a liquid sample within the passageway 72 by capillary action, despite opposing forces such as gravity. In one instance, the passageway 52 of the second body 40 additionally, or alternatively, comprises a dimension sufficiently small to enable holding a liquid sample within the passageway 52 by capillary action.

Figure 3:
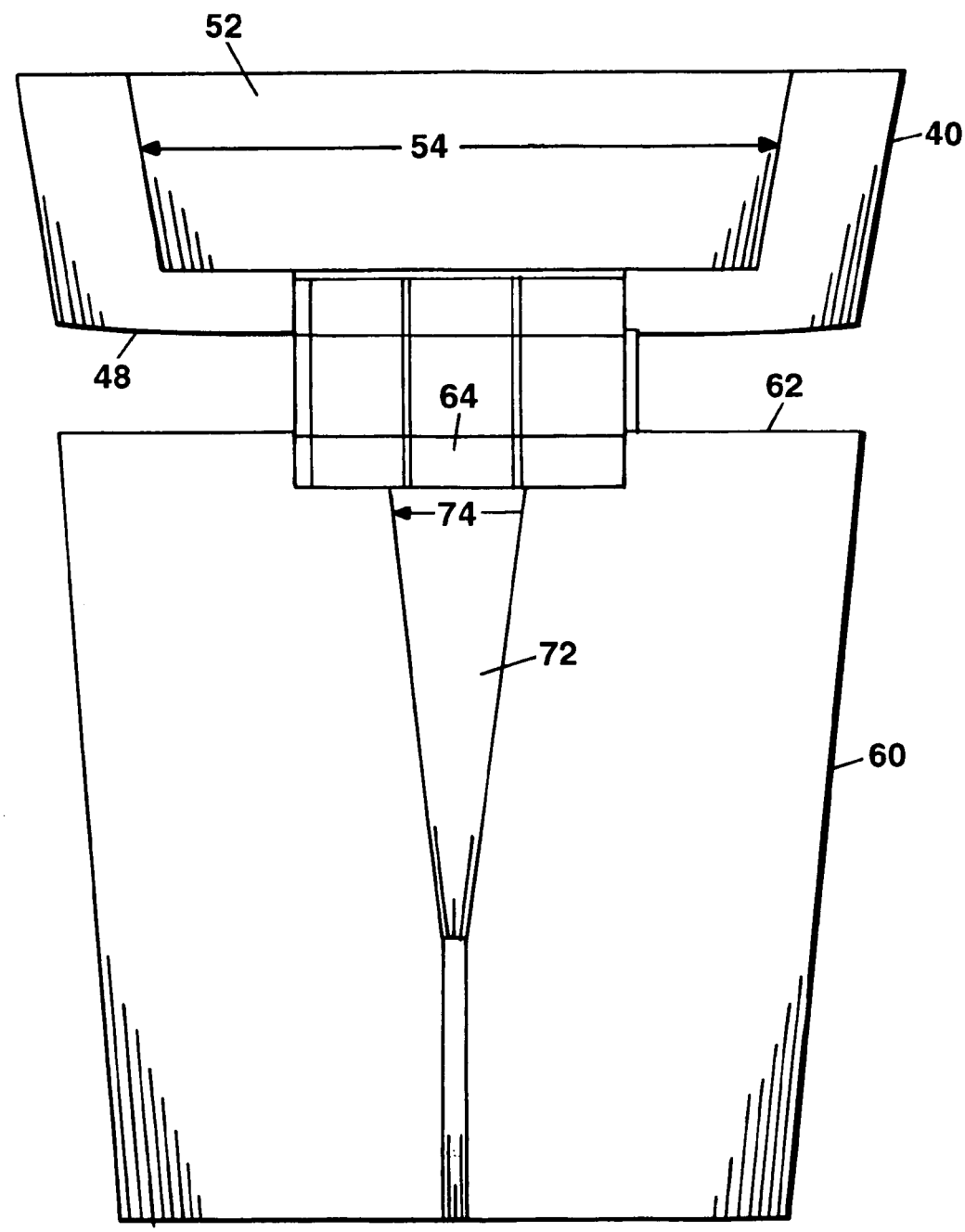
FIG. 3 is a schematic representation of a view of one embodiment of the interface between bodies in the embodiment shown in FIG. 1.

In another instance, shown in FIG. 3, at an end of the second body 40 that is operatively connected to the third body 60, a characteristic dimension 54 of the passageway 52 of the second body 40 is larger than a characteristic dimension 74, at the end 62 of the third body 60 that is operatively connected to the second body 40, of the passageway 72 of the third body 60. FIG. 3 depicts the interface between the second body 40 and the third body 60 and show the connection between the bodies and the small size of the inner bore of the passageway 72 of the third body 60.

In yet another instance, the passageway 52 of the second body 40 (body used for optical measurement) can be designed to have a larger dimension (bore) than the dimension of the passageways 32, 52 of the bodies 20, 60 on either side (or on one side) to minimize the fluid volume in the passageway 52.

In still another embodiment, at the interface between first body 20 (top module) and the second body 40 (also referred to as the optical module), the difference between a characteristic dimension of the first body 20 and a characteristic dimension of the second body 40 is such that the interface acts as a stop junction (also referred to as a capillary break or capillary stop junction), (i.e., the capillary force in the passageway 52 of the second body 40 is sufficient to induce flow while the capillary force in the passageway 32 of the first body 20 is not sufficient to induce flow) thereby limiting the amount of fluid that enters the apparatus. Because fluid will not pass this point by capillary action alone, some other source of fluid pressure is needed to move the fluid into the new region. This may be desirable to minimize the fluid quantity introduced into the apparatus, especially in an apparatus filled by capillarity alone.

Figure 4:
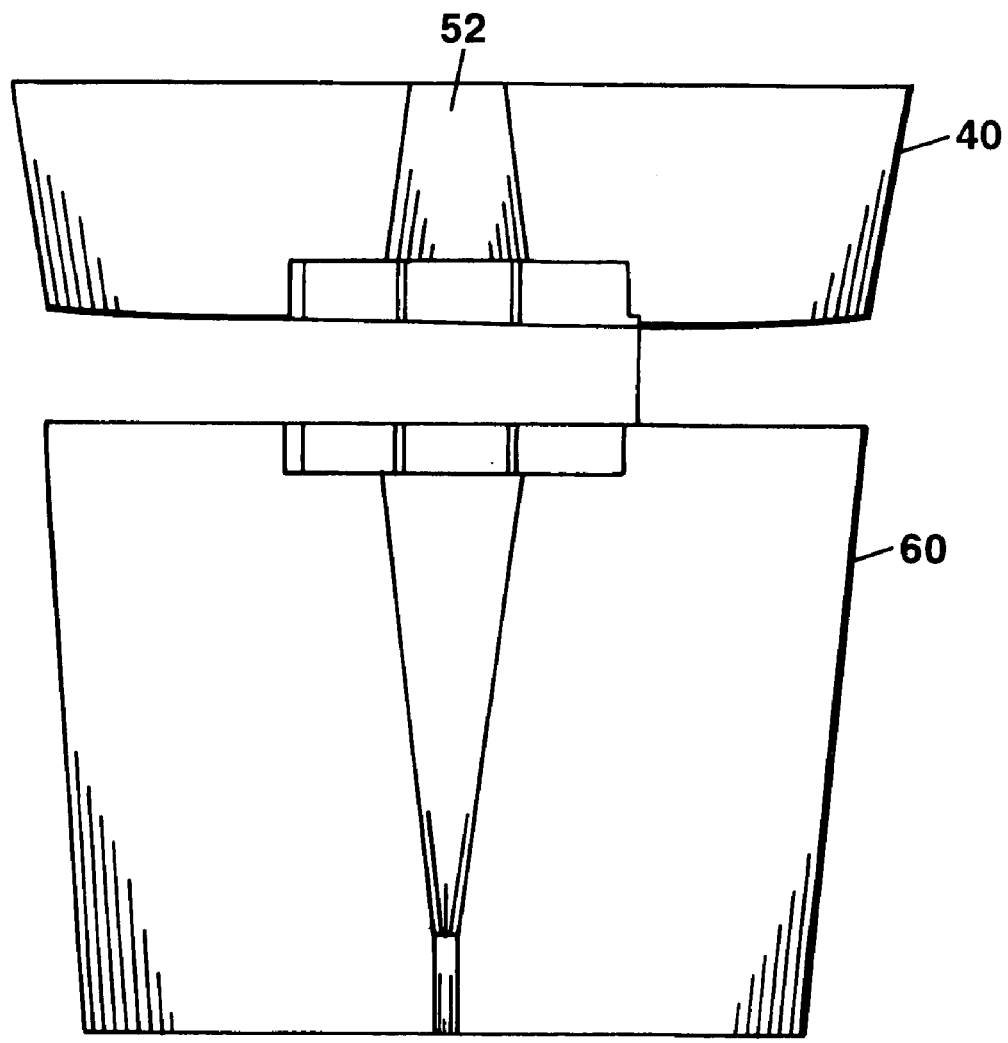
FIG. 4 is a schematic representation of a view of another embodiment of the interface between bodies in the embodiment shown in FIG. 1.

In a further embodiment, shown in FIG. 4, an alternative internal configuration of the interface between the second body 40 and the third body 60 limits internal volume in the passageway 52 but does not rely on a capillary stop junction to control the fluid flow.

In one aspect, at least a portion of the second body 40 is comprised of a material capable of allowing transmission of electromagnetic radiation of sufficient intensity to enable performance of an optical measurement (e.g., the material is a semi-transparent or a transparent material). Materials used to form the at least partially transparent portion(s) of the body may vary and may include any at least partially transparent material, for example, a polymeric material such as polyimide, polycarbonate, polystyrene, polyolefin, fluoropolymer, polyester, a nonaromatic hydrocarbon, polyvinylidene chloride, polyhalocarbon, such as polycholortrifluoroethylene. Polyolefins may include polyethylenes, polymethylpentenes and polypropylenes, and fluoropolymers may include polyvinyl fluorides. Other materials glass, quartz, silica, silicon rubber, such as crosslinked dimethyldisiloxane, or materials used in optical crystals, such as sapphire or garnet (e.g., undoped Yttrium Aluminum Garnet). In certain aspects, the material transmits light with a range of about 200-1100 nm, from about 180-1000 nm, and/or transmits light of a wavelength greater than about 900 nm. In other aspects, materials and dimensions are selected to ensure that a measured signal relating to a sample within the second body 40 remains within the limit of the linear range for measurements by a particular detection device with which the apparatus of this invention is used (e.g., such as a spectrophotometer, photometer, spectrofluorometer, and the like).

In one embodiment, there is a plurality of second bodies operatively connected to at least one other body of the apparatus. In one aspect, at least two of the plurality of second bodies comprises different properties, e.g, such as different optical properties or different abilities to transmit light. For example, in one aspect, one second body transmits UV and/or visible light, while another transmits fluorescent light.

Figure 5:
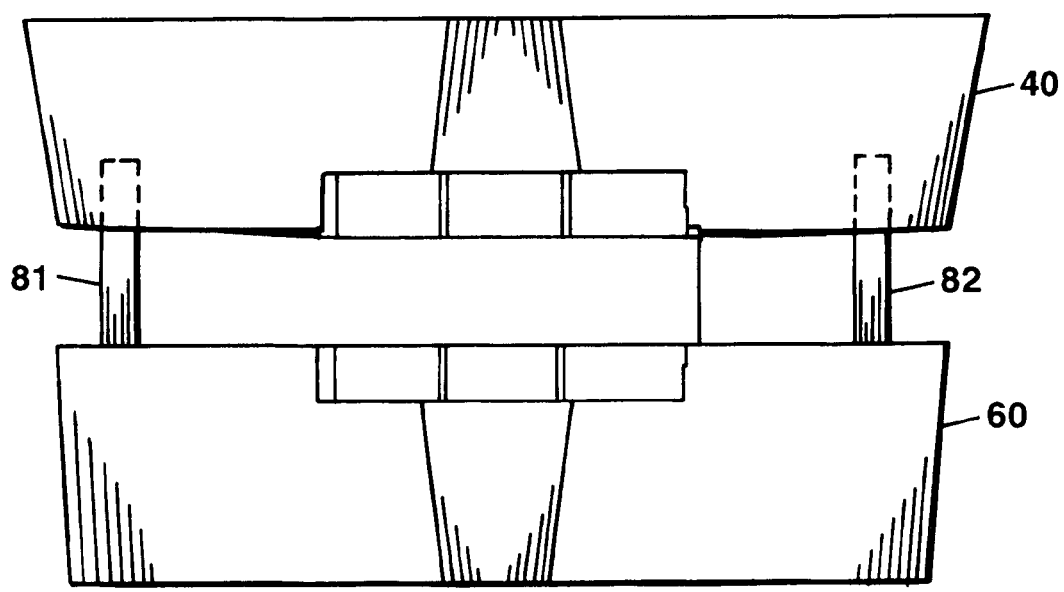
FIG. 5 is a schematic representation of one embodiment of the operative connection between bodies in the embodiment shown in FIG. 1.

The operative connection between the bodies 20, 40, 60 can have a number of possible embodiments. In one embodiment, the second body 40 (the optical module) may be insert injection molded into the other bodies 20, 60. In another embodiment, as shown in FIG. 5, the outer two bodies 20, 60 may capture the second body 40 (the optical module) between tabs 81, 82 that are bonded or welded together (e,g, using ultrasound, solvents, etc). In an alternative embodiment, the separate bodies may be adhesive bonded together using an appropriate surface treatment if necessary. Tabs may also be snap fit into an appropriately configured interface.

In the embodiment of the apparatus of this invention shown in FIG. 1, the material used for each body 20, 40, 60 may be different in order to optimize separately the material used in each body with respect to the intended function of each body (for example, sample acquisition, optical measurement, interface at the device for aspirating fluid). The interface of the bodies 20, 40, 60 may be optimized separately. For example, but not limited to, a stop junction can be introduced to effect a capillary break, or the passageways 32, 52, 72 in each body designed to minimize the fluid held in the channel formed by the three passageways.

In the embodiment of the apparatus of this invention shown in FIG. 1, each body 20, 40, 60 can be optimized so as to function independently. In one instance, the first body 20 can include a means for interfacing to an optical measurement device such as a spectrophotometer. (In one instance the interfacing means comprise an element or design condition that allows securely attaching the first body 20 to the optical measurement device. In one embodiment, but not limited only to this embodiment, the outer surface of the first body 20 is adapted to be securely held by a clamping component in the spectrophotometer. in another embodiment, the first body 20 is adapted to be attached to a holding component in the spectrophotometer.) In another instance, the first body 20 includes means for connecting or linking or snap-fitting to the first body of another apparatus of this invention in order to enable the substantially simultaneous selection of multiple samples (such as, for example, the tabs 81, 82 in FIG. 5). In a further instance, the second body 40 is designed to allow orientation with respect to a beam of electromagnetic radiation in order to enable alignment with respect to the beam in an optical instrument.

Figure 6:
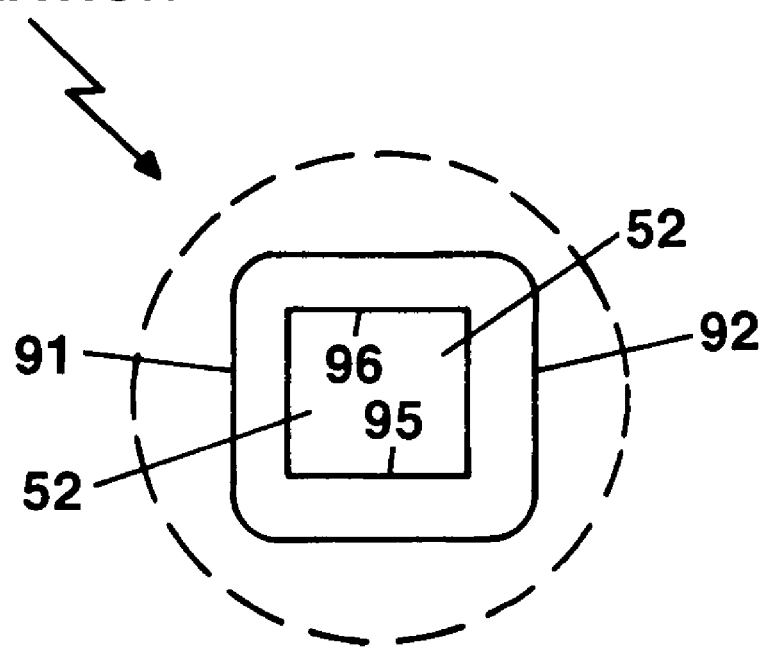
FIG. 6 is a schematic representation of a cross-sectional view of an embodiment of the second body in FIG. 1.

An embodiment of the second body 40 that would allow orientation with respect to a beam of electromagnetic radiation is shown in FIG. 6. The embodiment shown in FIG. 6 includes two planar outer surfaces 91, 92 that are substantially parallel to each other. In one embodiment, the two substantially planar outer surfaces 91, 92 allow orientation with respect to a beam of electromagnetic radiation. Also shown in FIG. 6 is an embodiment of a portion of the passageway 52 of the second body 40. In the embodiment shown in FIG. 6, a portion of the passageway 52 includes two planar surfaces 95, 96 forms a measurement region with a predetermined optical pathlength. Although in the embodiment shown in FIG. 6 the other two outer and inner surfaces are also planar, embodiments in which the other two outer and inner surfaces are not planar are also within the scope of this invention.

Figure 7:
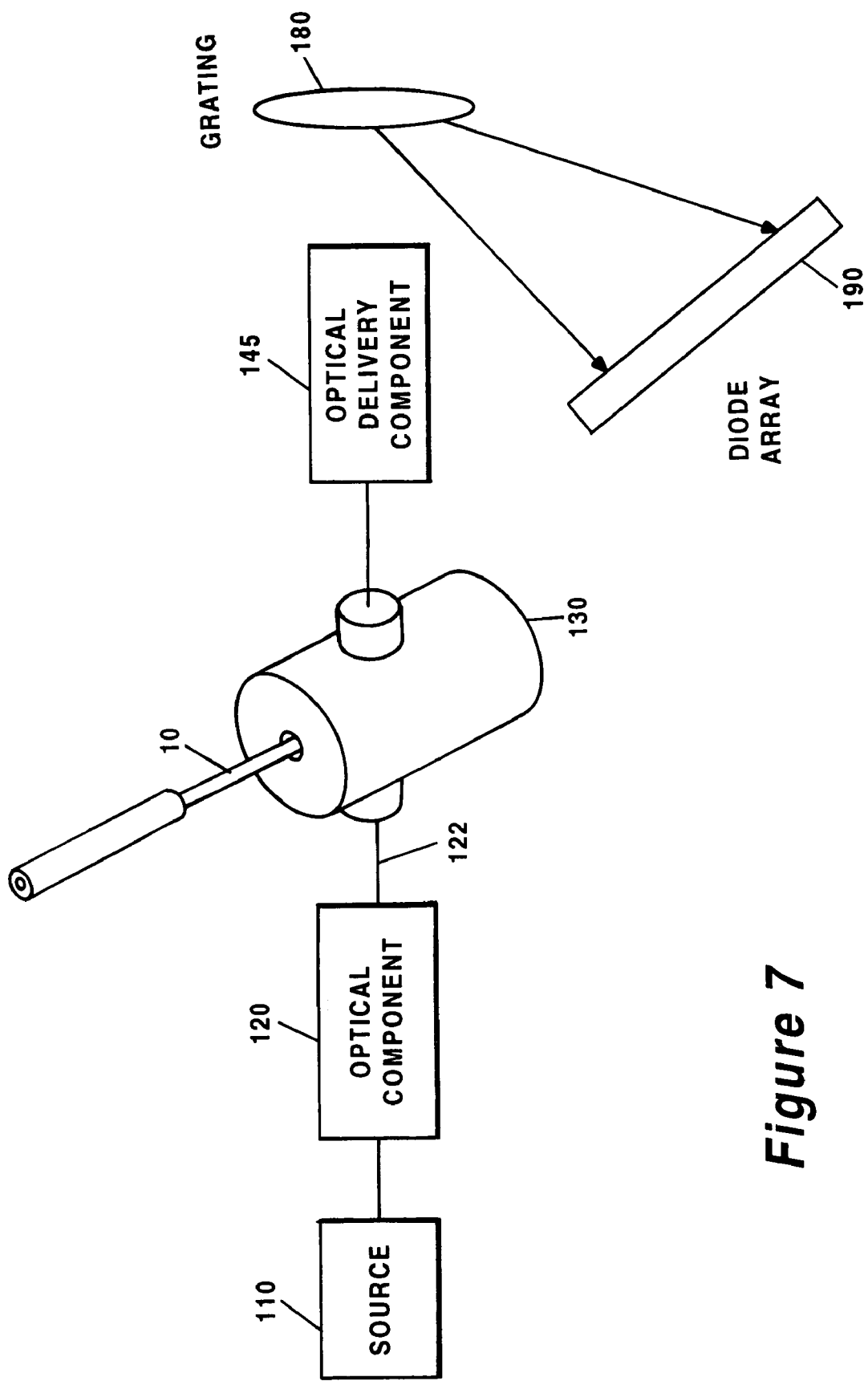
FIG. 7 is a schematic representation of a measurement system of this invention.

In one instance, the outer surface(s) of second body 40 and the inner surface(s) of the passageway 52 are not planar but a portion of the passageway 52 forms a measurement region with a predetermined optical pathlength for a given set of optical elements providing the beam of electromagnetic radiation. In that instance, the surfaces and materials are selected so that the measurement region has a predetermined optical pathlength when the given set of optical elements provides the beam of electromagnetic radiation, A measurement system capable of measuring a sample held by an embodiment of the apparatus of this invention is shown in FIG. 7. Referring to FIG. 7, the measurement system 100 includes a source of electromagnetic radiation 110 (also referred to as a light source), an optical component 120 capable of providing one or more beams 122 of electromagnetic radiation from the electromagnetic radiation originating from the source 110 (in one instance, the one or more beams 122 are provided by means of optical fibers), a holding component 130 capable of holding an embodiment 140 of the apparatus of this invention and of placing the embodiment 140 of the apparatus of this invention in the path of the one or more beams 122. The measurement system 100 also includes one or more optical delivery components 145, the optical delivery component being capable of receiving one or more beams after propagating through the apparatus 10 and the sample held therein. In the embodiment shown in FIG. 7, the optical delivery component 145 provides one or more beams to the detecting components of the measurement system. In FIG. 7, the detecting components are shown as the deflecting element 180 (a grating in one instance) and a detector array 190.

Figure 8A:
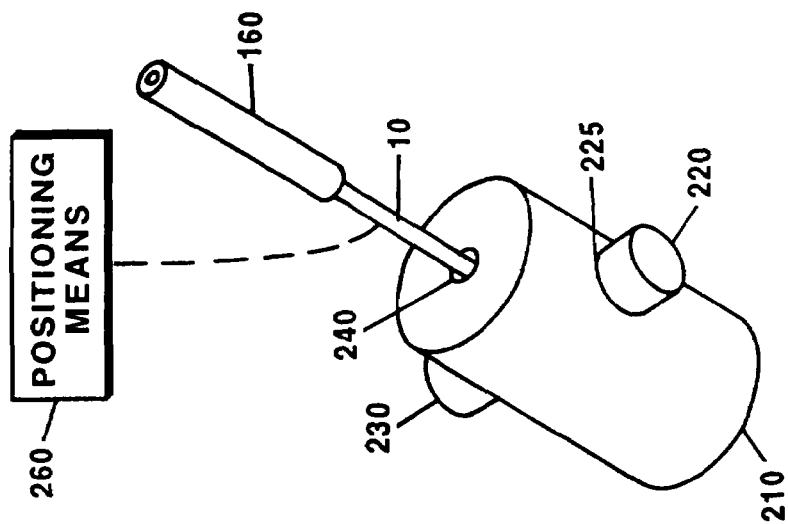
FIGS. 8a, 8b, 8c are schematic representations of a holding component in the measurement system of this invention.
Figure 8B:
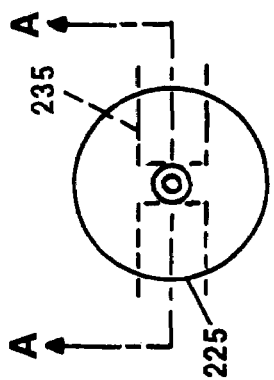
Figure 8C:
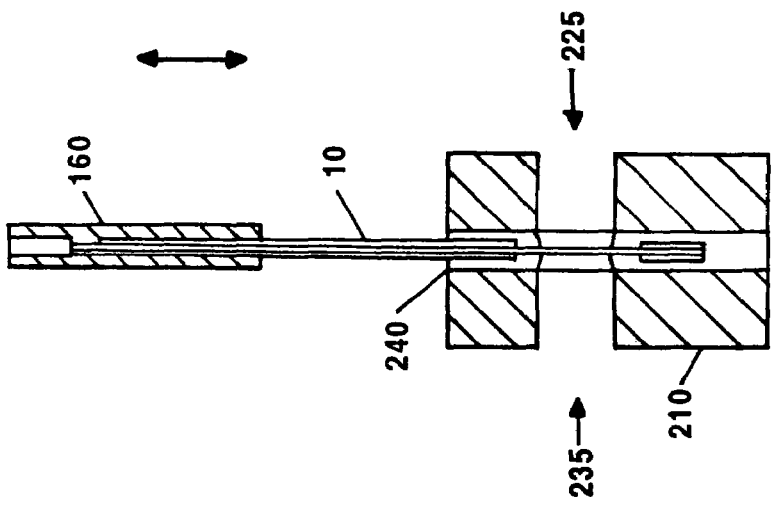

In one embodiment, the holding component 130 is the holder shown in FIGS. 8a, 8b and 8c. In one instance, the embodiment of the apparatus of this invention shown in FIG. 7 is the embodiment 10 of FIG. 1.

In one embodiment, the holding component 130 comprises a housing 210 capable of receiving an apparatus 10 and of holding the apparatus 10. The apparatus 10 is received by the housing 210 through a passageway 245. The housing shown in FIGS. 8a, 8b and 8c has at least one set of co-axial side openings 225, 235, an axis of the openings being perpendicular to the housing axis, the set of two openings being substantially aligned (that is, opening 325 is aligned with opening 335). In one aspect, the center of the optical window of the body is co-centered with the axis of the openings and the surface of an optical window is perpendicular to excitation light from a source light in an instrument in which the apparatus of this invention is used (e.g., such as a spectrophotomer). The one or more sets of openings 225, 235 in conjunction with the apparatus 10 define a transmission path for electromagnetic radiation when the apparatus 10 is held in the housing 210 and the openings are adapted to receive electromagnetic radiation.

In one embodiment, the housing 210 does not require focusing optics. In another embodiment, optical elements are used to account for the curved surfaces of the body and provide a predetermined pathlength. It should be noted that embodiments with more than one set of two openings are also within the scope of this invention.

In another embodiment, the openings 225, 235 are capable of receiving portions (e.g., such as ends) of optical waveguides such as fiber optic connectors. In that embodiment, which is shown in FIG. 8a, both source-side and detection-side optical fibers 220 and 230, respectively, are provided. Optical fibers as used herein may include collimating/collecting optics.

In certain aspects, an adaptor 240 may be used to interface the top face of the housing with the body of the apparatus to reduce stray light. The apparatus may be positioned within the housing 210 by manually pressing frictional or mechanical detents or by providing an automatic and/or motor-assisted element that can move in an appropriate direction (e.g., see, 260 in FIG. 8*a*), for example. Such frictional or mechanical detents and/or motor-assisted elements comprise exemplary representations of a securing component. The securing component positions the measurement region including at least one optical window in order to provide a transmission path.

In another embodiment of the holding component 130, the holding component 130 comprises a holding "sleeve" 160 that is capable of holding the apparatus 10 by frictional or mechanical detents. In one embodiment, the first body 20 of the apparatus 10 is adapted to enable the holding by frictional or mechanical detents. In one instance, the outer surface of the first body 20 has two planar sections that are parallel to each other and that facilitate the design of the frictional or mechanical detents. In another instance, the shape of the outer surface of the first body 20 is adapted to the frictional or mechanical detents.

Doing operation of the measurement system 100, at least a portion of an apparatus of this invention (such as, at least a portion of the second body 30 of the apparatus 10 of FIG. 1) is placed in a positional relation to the light source 110 and the detecting component 180 sourced at a light press is provided from the light source 110 to on optical detection device 190. The portion of the apparatus of this invention holds a liquid sample and by detecting an optical property, such as light absorbance if the measurement device is a spectrophotometer, properties of the sample can be obtained. By interfacing the first body 20 of the apparatus 10 of this invention with a device for aspirating fluids, the aspirating of the liquid sample into at least a portion of the second body 20 is enabled.

In one instance, the liquid sample comprises a nucleic acid, or peptides, polypeptides or proteins.

It should be noted that although one embodiment has been described in detail, embodiments in which the measurement device includes more than one optical path through the sample, more than one beam, and more than one optical delivery system are within the scope of this invention. Embodiments in which the apparatus of this invention has more than one section in the second body, where each section provides one predetermined optical path (as for example, the instance in which the second body has two sections, is section having two planar sides) are also within the scope of this invention. It should also be noted that a predetermined optical path can be obtained by many different embodiments. For example, a predetermined optical press can be obtained by having two planar sides in a portion of the second body or can also be obtained by selecting the materials and geometry (shape) of a portion of the second body so that the materials and geometry provide a predetermined optical path for a given optical illumination.

Although the invention has been described with respect to various embodiments, it should be realized this invention is also capable of a wide variety of further and other embodiments within the spirit and scope of the appended claims.

What is claimed is:

1. An apparatus for acquisition of a liquid sample, the apparatus comprising:
    a first body having openings at opposite ends of said first body;
    a second body having openings at opposite ends of said second body;
    a third body having openings at opposite ends of said third body;
    each of said first body, second body, and third body having a respective passageway connecting the openings at opposite ends thereof;
    at least a portion of a surface of said second body being at least partially transparent to predetermined electromagnetic radiation;
    said first body being operatively connected to said second body and said second body being operatively connected to said third body to permit flow of a liquid through the respective passageways thereof;
    at least a portion of said third body being adapted to enable acquisition of the liquid sample from a sample container;
    at least one of at least a portion of said passageway of said third body and at least a portion of said passageway of said second body being dimensioned to enable holding the liquid sample after retracting the apparatus from the sample container.

2. The apparatus of claim 1 wherein at least a portion of said passageway of said third body is dimensioned to enable holding, by capillary action, the liquid sample within said portion of said passageway of said third body.

3. The apparatus of claim 2 wherein at least a portion of said passageway of said second body is dimensioned to enable holding, by capillary action, the liquid sample within said portion of said passageway of said second body.

4. The apparatus of claim 1 wherein, at an end of said second body that is operatively connected to said third body, a dimension of a passageway of said second body is larger than a dimension, at an end of said third body that is operatively connected to said second body, of said passageway of said third body.

5. The apparatus of claim 1 wherein a dimension of a passageway of said second body, at least one end of said second body, is smaller than at a midpoint of said passageway of said second body.

6. The apparatus of claim 1 wherein an end of said first body and an opening of said first body are capable of operatively connecting to a device for aspirating fluid.

7. The apparatus of claim 1 wherein said operative connections are substantially gastight connections.

8. The apparatus of claim 1 wherein at least a portion of said third body is comprised of a substantially hydrophobic material.

9. The apparatus of claim 1 wherein at least a portion of said third body is comprised of a substantially hydrophilic material.

10. The apparatus of claim 1 wherein said passageway of said second body comprises a measurement region with a predetermined optical pathlength.

11. An apparatus for acquisition of a liquid sample, the apparatus comprising:
    a first body having openings at opposite ends of said first body;
    a second body having openings at opposite ends of said second body;
    a third body having openings at opposite ends of said third body;
    each of said first body, second body, and third body having a respective passageway connecting the openings at opposite ends thereof;
    at least a portion of a surface of said second body being at least partially transparent to predetermined electromagnetic radiation;
    said first body being operatively connected to said second body and said second body being operatively connected to said third body to permit flow of a liquid through the respective passageways thereof;

at least a portion of said passageway of said third body being dimensioned to enable holding, by capillary action, the liquid sample within said portion of said passageway of said third body; and at least a portion of said passageway of said second body being dimensioned to enable holding, by capillary action, the liquid sample within said portion of said passageway of said second body;

a junction between an opening of said first body at an end of said first body that is operatively connected to said second body and an opening of said second body at an end of said second body that is operatively connected to said first body comprising a junction requiring an additional force besides capillary action in order to induce flow.

12. A method for providing an apparatus for holding a liquid sample, the method comprising the steps of:

providing a first section of the apparatus;

comprising a material at least partially transparent to electromagnetic radiation;

providing a second section of the apparatus having at least a portion of the second section comprising a material at least partially transparent to electromagnetic radiation;

operatively connecting an end of the first section to an end of the second section in order to permit flow of the sample between the first section and the second section;

providing a third section of the apparatus;

adapting at least a portion of the third section to enable acquisition of a fluid sample from a sample supply;

selecting dimensions of at least one of at least a portion of said passageway of said third body and at least a portion of said passageway of said second body in order to enable holding the liquid sample after retracting the apparatus from the sample container;

operatively connecting another end of the second section to an end of the third section in order to permit flow between the second section and the third section.

13. The method of claim 12 further comprising the step of selecting another material of preselected hydrophobicity; and wherein at least a portion of the third section is comprised of said another material.

14. The method of claim 13 further comprising the step of selecting yet another material; and wherein the first section is comprised of said yet another material.

15. The method of claim 12 further comprising the step of selecting another material; and wherein the first section is comprised of said another material.

16. A measurement system capable of measuring a liquid sample, the measurement system comprising:

a source of electromagnetic radiation;

an optical component capable of providing at least one beam of electromagnetic radiation from electromagnetic radiation originating from said source;

a component capable of holding an apparatus in a path of said at least one beam, said apparatus capable of holding a liquid sample comprising:

a first body having openings at opposite ends of said first body;

a second body having openings at opposite ends of said second body;

a third body having openings at opposite ends of said third body; at least a portion of said third body being adapted to enable acquisition of a liquid sample from a sample container;

each of said first body, second body, and third body having a respective passageway connecting the openings at opposite ends thereof;

at least one of at least a portion of said passageway of said third body and at least a portion of said passageway of said second body being dimensioned to enable holding the liquid sample after retracting the apparatus from the sample container;

at least a portion of a surface of said second body being at least partially transparent to predetermined electromagnetic radiation;

said passageway of said second body comprising a measurement region with a predetermined optical pathlength; and said first body being operatively connected to said second body and said second body being operatively connected to said third body to permit flow of a liquid through the respective passageways thereof; and at least one optical delivery component, said at least one optical delivery component disposed to receive said at least one beam after propagating through said apparatus; and a detecting component optically disposed to receive said at least one beam from at least one optical delivery component and capable of obtaining a desired measurement from said at least one beam.

17. The measurement system of claim 16 wherein at least a portion of said passageway of said third body is dimensioned to enable holding, by capillary action, the liquid sample within said portion of said passageway of said third body.

18. The measurement system of claim 17 wherein at least a portion of said passageway of said second body is dimensioned to enable holding, by capillary action, the liquid sample within said portion of said passageway of said second body.

19. The measurement system of claim 16 wherein, at an end of said second body that is operatively connected to said third body, a dimension of a passageway of said second body is larger than a dimension, at an end of said third body that is operatively connected to said second body, of said passageway of said third body.

20. The measurement system of claim 16 wherein a dimension of a passageway of said second body, at least one end of said second body, is smaller than at a midpoint of said passageway of said second body.

21. The measurement system of claim 16 wherein an end of said first body and an opening of said first body are capable of operatively connecting to a device for aspirating fluid.

22. A measurement system capable of measuring a liquid sample, the measurement system comprising:

a source of electromagnetic radiation;

an optical component capable of providing at least one beam of electromagnetic radiation from electromagnetic radiation originating from said source;

a component capable of holding an apparatus in a path of said at least one beam, said apparatus capable of holding a liquid sample and comprising:

a first body having openings at opposite ends of said first body;

a second body having openings at opposite ends of said second body;

a third body having openings at opposite ends of said third body;

each of said first body, second body, and third body having a respective passageway connecting the openings at opposite ends thereof;

at least a portion of a surface of said second body being at least partially transparent to predetermined electromagnetic radiation;

said passageway of said second body comprising a measurement region with a predetermined optical pathlength;

said first body being operatively connected to said second body and said second body being operatively connected to said third body to permit flow of a liquid through the respective passageways thereof;

at least one optical delivery component, said at least one optical delivery component disposed to receive said at least one beam after propagating through said apparatus; and a detecting component optically disposed to receive said at least one beam from at least one optical delivery component and capable of obtaining a desired measurement from said at least one beam;

at least a portion of said passageway of said third body being dimensioned to enable holding, by capillary action, a liquid sample within said portion of said passageway of said third body; and at least a portion of said passageway of said second body being dimensioned to enable holding, by capillary action, a liquid sample within said portion of said passageway of said second body;

a junction between an opening of said first body at an end of said first body that is operatively connected to said second body and an opening of said second body at an end of said second body that is operatively connected to said first body comprising a junction requiring an additional force besides capillary action in order to induce flow.

23. A method for measuring an optical property of a liquid sample, comprising the steps of:

providing an apparatus comprising:

a first body having openings at opposite ends of said first body;

a second body having openings at opposite ends of said second body;

a third body having openings at opposite ends of said third body;

each of said first body, second body, and third body having a respective passageway connecting the openings at opposite ends thereof;

at least a portion of a surface of said second body being at least partially transparent to predetermined electromagnetic radiation;

said passageway of said second body comprising a measurement region with a predetermined optical pathlength;

wherein at least a portion of said third body is adapted to enable acquisition of a liquid sample from a sample container;

at least one of at least a portion of said passageway of said third body and at least a portion of said passageway of said second body being dimensioned to enable holding the liquid sample after retracting the apparatus from the sample container; and said first body being operatively connected to said second body and said second body being operatively connected to said third body to permit flow of a liquid through the respective passageways thereof;

placing at least a portion of the second body in a positional relationship to a light source and detector of an optical detection device such that a light path is provided from the light source through the at least a portion of the second body, to the optical detection device, wherein the at least a portion of the second body holds the liquid sample.

24. The method of claim 23 further comprising the steps of:

interfacing the first body with a device for aspirating fluid; and aspirating the liquid sample into the at least a portion of the second body.

25. The method of claim 24, wherein the liquid sample comprises a nucleic acid.

26. The method of claim 24, wherein the liquid sample comprises peptides, polypeptides, or proteins.

27. The method of claim 24, wherein the optical property is correlated with a concentration of a biomolecule in the liquid sample.

28. The method of claim 23, wherein the optical detection device is a spectrophotometer.

29. The method of claim 23, wherein the optical property is light absorbance.

* * * * *